US005475129A

United States Patent [19]
Burke, Jr. et al.

[11] Patent Number: 5,475,129
[45] Date of Patent: Dec. 12, 1995

[54] PHOSPHONOALKYL PHENYLALANINE COMPOUNDS SUITABLY PROTECTED FOR USE IN PEPTIDE SYNTHESIS

[75] Inventors: Terrence R. Burke, Jr., Bethesda; Mark S. Smyth, Rockville; Benjamin B. Lim, Baltimore, all of Md.

[73] Assignee: The United States of America as represented by the Department of Health and Human Services, Washington, D.C.

[21] Appl. No.: 73,088

[22] Filed: Jun. 8, 1993

Related U.S. Application Data

[63] Continuation-in-part of Ser. No. 897,391, Jun. 12, 1992, Pat. No. 5,264,607, and a continuation-in-part of Ser. No. 767,621, Sep. 30, 1991, Pat. No. 5,200,546.

[51] Int. Cl.$^6$ .................................................. C07F 9/40
[52] U.S. Cl. ............................................................ 558/190
[58] Field of Search ............................................... 558/190

[56] References Cited

U.S. PATENT DOCUMENTS

| | | | |
|---|---|---|---|
| 4,657,899 | 4/1987 | Rzeszotarski . | |
| 5,190,921 | 3/1993 | Roques et al. | 514/17 |
| 5,200,546 | 4/1993 | Burke, Jr. et al. | 558/190 |
| 5,264,607 | 11/1993 | Burke, Jr. et al. | 558/141 |

FOREIGN PATENT DOCUMENTS 2198134  6/1988  United Kingdom .

OTHER PUBLICATIONS

Paquet, A., Can. J. Chem., 1982, (60), pp. 976–980.
Banert, K., Tetrahedron Lett., 1985, 26(43), pp. 5261–5264.
Carey, et al., Advanced Organic Chemistry; 2nd Ed., 1983, p. 193.
Streitwieser, et al., Introduction to Organic Chemistry; 3rd Ed., 1985, pp. 737–738.
Fessenden, et al., Organic Chemistry, 1979, p. 507.
Blackburn, et al., J. Chem. Soc., 1986, pp. 913–917.
Ackerman, et al., J. Am. Chem. Soc., 1956, (78), pp. 4444–4447.
Berlin, et al., J. Org. Chem., 1965, (30), pp. 1265–1267.
Berlin, et al., Anal. Chem., 1969, (41), pp. 1554–1559.
Gazizov, et al., Zh. Obshch, Khim, 1970, (48), pp. 31–32.
Pahinkin, et al., Zh. Obshch. Khim, 1970, (48), pp. 28–30.
Terauchi, et al., Bull. Chem. Soc. Jpn., 1970, (43), pp. 883–890.
Sekine, et al., J. Org. Chem., 1980, (45), pp. 4162–4167.
Sekine, et al., Tetrahedron Lett., 1981, (22), pp. 3617–3620.
Sekine, et al., Chem. Lett., 1981, p. 1087.
Kume, et al., J. Org. Chem., 1984, (49), pp. 2139–2143.
Fujii, et al., Tetrahedron Lett., 1986, (26), pp. 3365–3368.
Fujii, et al., Tetrahedron, 1987, (43), pp. 3395–3407.
Middleton, et al., J. Org. Chem., 1988, (45), pp. 2883–2887.
March, J., Advanced Organic Chemistry, 1985, 3rd Ed., p. 389.
Weast, R. C., ed. Handbook of Chem. and Phys., 1979, pp. F–231–235.
Berlin, et al., J. Am. Chem. Soc., 1964, (86), pp. 3862–3866.
Burke, et al., Synthesis, 1991, pp. 1019–1020.
Middleton, W. J., J. Org. Chem., 1975, (40), pp. 574–578.
M. Hudlicky, Org. Reactions, 1988, (35), pp. 513–637.
Blackburn, G. M., et al., J. Chem. Soc. Perkin Trans. I., 1984, pp. 1119–1125.
Bozell J. J., et al., J. Org. Chem., 1991, (56), pp. 2584–2587.
Glebova, Z. I., et al., Zh Obshch Khim., 1985, (55), pp. 1435–1437.
Hartman, G. D., et al., Syn. Comm., 1991, (21), pp. 2103–2107.
Cushman, M. et al. *Tetrahedron Letters* 33(9), 1193–1196 (issued Feb. 25, 1992).
Garbay–Jaureguiberry, C. et al. *Tetrahedron: Asymmetry* 3(5), 637–650 (issued May 1992).
Wrobel, J. et al. *Tetrahedron Letters* 34(22), 3543–3546 (Issued may 28, 1993).
Greene, T. W. *Protective Groups in Organic Synthesis* John Wiley and sons: New York, 1981; pp. 218–224.

*Primary Examiner*—Johann Richter
*Assistant Examiner*—M. G. Ambrose
*Attorney, Agent, or Firm*—Birch, Stewart, Kolasch & Birch

[57] ABSTRACT

The disclosure is concerned with providing phosphonic acid-containing derivatives of phenylalanine and optically active isomers thereof, which are functionalized in a manner which makes them suitable for facile incorporation into peptides using standard solid-phase or solution-phase techniques.

3 Claims, No Drawings

PHOSPHONOALKYL PHENYLALANINE COMPOUNDS SUITABLY PROTECTED FOR USE IN PEPTIDE SYNTHESIS

The present U.S. patent application is a continuation-in-part of U.S. patent application Ser. No. 07/897,391, filed on Jun. 12, 1992, now U.S. Pat. No. 5,264,607, and a continuation-in-part of Ser. No. 07/767,621 now U.S. Pat. No. 5,200,546, filed on Sep. 30, 1991, both of which are incorporated herein by reference in their entirety.

FIELD OF THE INVENTION

The present invention is concerned with providing phosphonic acid-containing derivatives of phenylalanine and optically active isomers thereof, which are functionalized in a manner which makes them suitable for facile incorporation into peptides using standard solid-phase or solution-phase techniques. The present invention is also concerned with providing an advantageous one-step reaction method for preparing benzylic α,α-difluorophosphonates from corresponding benzylic ketophosphonates, and with a one-step method of preparing phosphonomethyl substituted phenylalanine compounds by hydrogenating appropriately substituted α-azido cinnamic acid derivatives.

BACKGROUND OF THE INVENTION

Synthesis of 4-phosphonomethyl-DL-phenylalanine (Formula 1a), and derivatives thereof (Formulas 1b–d) have previously been reported[1–4] (See Table 1). The purposes of such preparations were to utilize the prepared 4-phosphonomethyl-DL-phenylalanines as competitive antagonists of N-methyl-D-aspartic acid[2] or as mimics of O-phosphotyrosine[1,3,4]. These previously prepared derivatives are not suitable for facile incorporation into peptides or peptide mimetics using standard protocols developed for either solution-phase or solid-phase peptide synthesis using "Fmoc protocols"[5,6].

Central to peptide synthesis is the protection of reactive functional groups with moieties which are easily removed under conditions which are compatible with the preservation of other functionalities in the peptide. A major branch of peptide chemistry has recently evolved using 9-fluorenylmethyloxycarbonyl (Fmoc) groups for protection of α-amino groups during coupling reactions of amino acid monomers into peptide chains. The Fmoc groups are then generally removed by brief treatment with an appropriate base such as piperidine. In such reactions, other chemically reactive groups on the amino acid monomers must be protected by functionalities which are stable to the basic conditions utilized to remove Fmoc groups. Traditionally, these other groups were removed by mild acid treatment (e.g., trifluoroacetic acid) such as used to cleave the finished peptide from a given resin. The tert-butyl group is used widely in Fmoc-bearing residues for the protection of hydroxyl groups, since it is stable to base and easily removed by mild acid treatment. Unlike the present inventive compounds, the prior known 4-phosphonomethyl-DL-phenyl-alanine compounds shown in Table 1 (Compounds 1a–1d) require significant synthetic manipulation to render them suitable for peptide synthesis.

Previously, non-benzylic α-fluorophosphonates have been converted to α,α-difluorophosphonates using electrophilic fluorinating reagents[10], and benzylic α-fluorophosphonates have been prepared from α-hydroxyphosphonates using (diethylamino)sulfur trifluoride (DAST)[13]. The conversion of α-oxoarylacetates to α,α-difluoroarylacetates using DAST[11] has also been reported.

TABLE 1

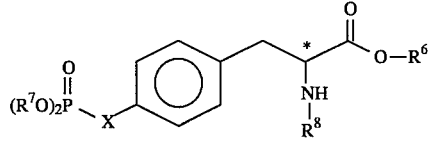

| | $R^1$ | $R^2$ | $R^3$ | Ref |
|---|---|---|---|---|
| 1a | H | H | OH | 1,2,3,4 |
| 1b | Et | Bz[a] | OH | 1 |
| 1c | Et | Ac | OMe | 2 |
| 1d | H | H | HNBn[b] | 4 |

[a]Bz = benzoyl
[b]Bn = benzyl

SUMMARY OF THE INVENTION

The present invention provides novel 4-phosphonomethyl-DL-phenylalanine derivatives, analogues thereof and optical isomers thereof of the following formula:

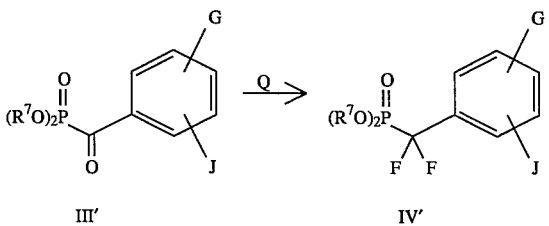

wherein X is —$CH_2$—, —CHF—, —$CF_2$—, —CHOH— or —C(O)—; $R^6$ is hydrogen, benzyl, pentafluorophenyl, nitrophenyl, 1-benzotriazolyl, 1-succinimidoyl or methyl, $R^7$ is $C_{1-8}$ lower alkyl (e.g., methyl, ethyl, propyl, isopropyl, tertiary butoxy, etc.); $R^8$ is Fmoc (i.e., 9-fluorenylmethyloxycarbonyl) or Boc (i.e., tertiary butoxycarbonyl); and * indicates a chiral carbon atom.

The compounds of Formula (I) are useful in peptide synthesis. More particularly, they are useful in preparing peptides wherein one wishes to obtain stable analogues of O-phosphotyrosine which are useful as molecular tools in biochemical studies and/or as therapeutic agents in the treatment of certain proliferative diseases.

We also provide herein an advantageous one-step reaction method for preparing benzylic α,α-difluorophosphonates of Formula IV' from corresponding benzylic ketophosphonates of Formula III'. The method is as follows:

wherein:

$R^7$ is $C_{1-8}$ lower alkyl;

G and J are the same or different and are non-reaction interfering moieties; and Q is a nucleophilic fluorinating agent, e.g., (diethylamino)sulfur trifluoride (DAST) or the like.

Like the compounds of Formula (I), the compounds of Formula (IV') are useful in peptide synthesis. More specifically, they are useful in preparing peptides wherein one wishes to obtain stable analogues of O-phosphotyrosine which are useful as molecular tools in biochemical studies and/or as therapeutic agents in the treatment of certain proliferative diseases.

The present invention is also concerned with providing a novel synthesis process wherein an azide derivative of Formula III is converted into the corresponding amide derivatives of Formula II, as shown in the following Reaction Scheme I.

Reaction Scheme I

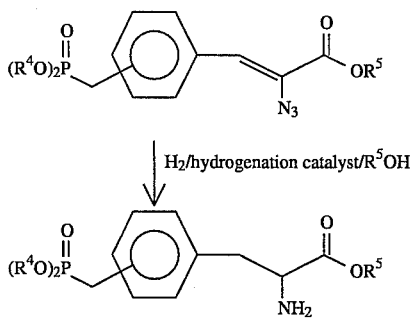

In the above Reaction Scheme I, $R^4$ and $R^5$ are the same or different and are selected from the group consisting of $C_{1-8}$ lower alkyl (e.g., methyl, ethyl, propyl, 2-propyl, butyl, t-butyl, and the like), and the hydrogenation catalyst is 10% Pd.C, or platinum, or the like. The compounds are useful as intermediates in forming certain of the Formula I compounds discussed herein.

The present invention is also concerned with another novel synthesis process which may be used in preparing certain compounds of Formula I, and certain related derivatives. This synthesis process is shown below in Reaction Scheme II, and encompasses as one of its steps the synthesis process outlined in Reaction Scheme I.

Reaction Scheme II.

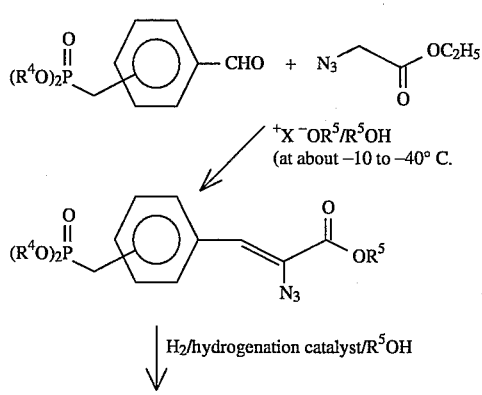

-continued
Reaction Scheme II.

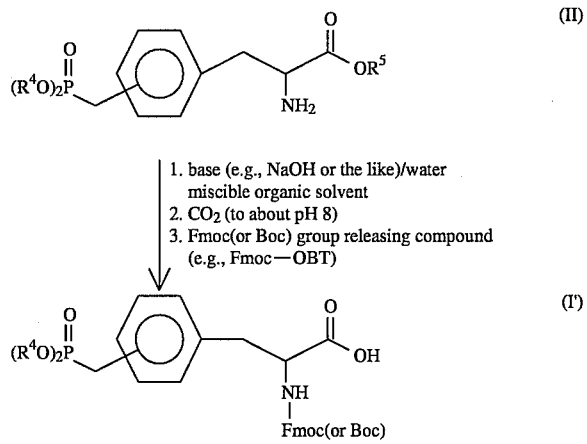

In the above Reaction Scheme (II), $R^4$ and $R^5$ are $C_{1-8}$ lower alkyl, (e.g., methyl, ethyl, propyl, butyl, pentyl, hexyl, octyl, 2-propyl, t-butyl, and the like), $X^+$ is an alkali metal such as sodium or the like; the hydrogenation catalyst is 10% Pd.C, platinum or the like, the water miscible organic solvent is dioxane, an alcohol (e.g., methanol, ethanol, etc.), acetonitrile or the like, Fmoc-OBT is 1-benzo-triazolyl-9-fluorenylmethyloxy carbonate, and Fmoc is 9-fluoronylmethyloxycarbonyl. The compound 1-succin-imidoly-9-fluorenylmethyl carbonate, or another suitable compound which is capable of releasing either a Fmoc or Boc group, may be used in the above reaction scheme in place of Fmoc-OBT, if so desired.

The compounds of Formula (I') shown in Reaction Scheme II above may be reacted with an appropriate $R^6$ moiety to form the analogous Formula (I) compound wherein $R^6$ is other than hydrogen. Such reactions are readily known by those skilled in the art and include, for example, reacting a Formula I' compound with carbonyldiimidazole (DCC) prior to reacting the same with an appropriate $R^6$ moiety.

The present invention is also concerned with providing compounds encompassed by Formula VI.

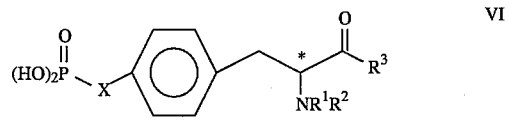

wherein X' is —CHOH—, —CHF—, —$CF_2$—, or —C(O)—; $R^1$ and $R^2$ are selected from the group consisting of H, $C_{1-8}$ lower alkyl, $C_{6-12}$ aryl, acyl, carbamoyl and urethanyl; $R^3$ is $OR^4$ or —$NR^1R^2$, where $R^4$ is $C_{1-8}$ lower alkyl, $C_{6-12}$ aryl, acyl or carbamoyl; and * denotes a chiral carbon atom which encompasses D and L isomers thereof as well as racemic mixtures thereof.

The compounds of structure VI are potentially useful as therapeutic agents and/or as molecular tools, e.g., they can be incorporated into peptides having anti-cancer activity.

DETAILED DESCRIPTION OF THE INVENTION

The following description and Example sections are provided to further aid those desiring to practice the present invention. Even so, the following sections are not to be construed as limiting to the scope of protection afforded to the present inventors in their discoveries.

As indicated in the Summary of the Invention section hereof, the present invention is concerned with providing novel 4-phosphonomethyl-DL-phenylalanine derivatives and analogues thereof, and also concerned with providing an advantageous one-step method for preparing benzylic α,α-difluorophosphonates of Formula IV' from the corresponding benzylic ketophosphonates of Formula III'. General considerations concerning each of these inventions are provided below, and thereafter, Examples relating to compounds of Formula I and their preparation as well as the inventive methods hereof, are provided.

In U.S. patent application Ser. No. 07/879,391, filed Jun. 12, 1992, and Ser. No. 07/767,621 filed on Sep. 30, 1991, methods are provided for preparing certain of the above Formula I compounds (wherein $R^7$ is tertiary butyl, and $R^8$ is Fmoc). The methods taught therein are thus applicable and are desirable in preparing certain of the present inventive compounds. This is, for example, true with respect to the compounds of Formula I, wherein X is —$CF_2$—. This is due to the fact that the inventors have discovered a new and highly advantageous method for preparing such compounds.

As shown in the Summary of the Invention section hereof, the present inventors can produce benzylic difluorophosphonates of Formula IV' from benzylic α-oxophosphonates of Formula III'. The reaction method is simple and advantageous. Specifically, a compound of Formula III' is fluorinated with a nucleophilic fluorinating agent such as (diethylamino)sulfur trifluoride. However, other nucleophilic fluorinating agents may also be used if desired. In one preferred embodiment of the present invention, compounds of Formula III' are reacted under neat conditions at room temperature (about 20°–25° C.) with DAST. However, these preferred reaction conditions should not be deemed to unduly limit the present inventive discovery. The following Examples II, III and VI are exemplary of the advantageous fluorination process provided, when a compound of Formula III' is converted to a compound of Formula IV' in a single step.

Each of the compounds of Formula III' and IV' may be substituted with substituents G and J as described above. Each of these substituents must be a non-reaction interfering moiety. Exemplary of such moieties are groups which do not adversely affect the presence of the $R^7$ lower alkyl groups substituting the phosphorous atom. For example, substituents G and J should not be acidic substituents, or hydroxy substituted alkyls or alcohols or ketones or aldehydes in their free form. However, ester moieties may be utilized if so desired, and exemplary of suitable non-interfering substituents for G and J are hydrogen, halogen (F, Cl, Br and I), $C_{1-8}$ alkyl, halogen substituted $C_{1-8}$ alkyl, and other accepted groups such as provided for in the Examples hereof.

Regarding the preparation of compounds of Formula III', α-oxophosphonates are normally prepared by the Michaelis-Arbuzov reaction of acyl chlorides with trialkyl phosphites, [17,18]. Nonetheless, we found that high yields of the desired α-oxophosphonates of Formula III' can be obtained by the oxidation of corresponding α-hydroxyphosphonates of Formula II' employing a variety of oxidizing agents, but preferably mild oxidation conditions employing activated DMSO methodologies such as Swern oxidations, when $R^7$ is other than tert-butyl.

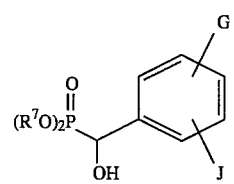

In Formula II' G and J are the same or different and are non-reaction interfering moieties as defined above with respect to Formula IV', however, with the additional consideration that G and J may contain an unprotected tertiary hydroxy substituent.

In proceeding from a compound of Formula II' to III', $MnO_2$ provided high yields of the desired α-oxophosphonates when $R^7$ was tertiary butyl. However, other oxidizing agents including pyridinium dichromate, pyridinium chlorochromate, dichloro dicyanobenzoquinone (DDQ) and Swern oxidation were also found to yield the desired α-oxophosphonates of Formula III'. Swern oxidations are especially useful for preparing compounds wherein $R^7$ is ethyl, as well as other $C_{1-8}$ lower alkyl moieties.

Generally, we note that when phosphite esters other than tertiary-butyl (i.e., ethyl) were utilized instead of the t-butyl substituent occurring on compounds of Formula II', such groups were incompatible with the reaction transformation, unless mild oxidation conditions were utilized. Specifically, when $R^7$ was methyl or benzyl, and $MnO_2$ was the oxidizing agent utilized, a reversion of the hydroxyphosphonate to the aldehyde resulted. Additionally, we note that an oxidizing method of preparing compounds of Formula III' requires that G and J not be hydroxy groups or hydroxy substituted moieties (other than tertiary hydroxy) during oxidation of the corresponding α-hydroxyphosphonate. However, G and J may contain protected hydroxy substituents if desired, which are later deprotected (after oxidation of the α-hydroxyphosphonate) to give a Formula III' compound having a G and/or J substituent comprising a hydroxy or hydroxy substituted moiety.

EXAMPLES

The following Examples are provided to illustrate certain embodiments and advantages associated with the present discoveries.

Specifically regarding each of the Examples provided below, the following comments are thought appropriate.

Example I

As indicated in the Example, central to the synthesis of the compound provided is the aldol condensation of ethyl α-azidoacetate with 4-[bis(tert-butyl)phosphonomethyl]-benzaldehyde to yield vinyl azide. The synthesis method provided in Example I, as well as those provided in U.S. patent application Ser. No. 07/767,621, filed on Sep. 30, 1991, provide the basis for many of the other reactions set forth in the present application.

Example II

This Example provides a general process for the synthesis of benzylic difluorophosphonates. In the Example, each of G and J are hydrogen. However, this should not be deemed to limit the present inventive discovery since G and J may be other non-reaction interfering moieties, if so desired.

Regarding the procedure utilized in Example II, we initially sought to prepare benzylic α,α-difluorophosphonates from the corresponding benzylic α-hydroxyphosphonates through the intermediacy of the α-fluorophosphates. While this appeared particularly appealing since benzylic α-hydroxyphosphonates are easily obtained by the reaction of aldehydes with dialkyl phosphites under alkaline conditions[12], we were unable to convert the benzylic monofluoro to the difluorophosphonates by this approach. Based on this fact, we postulated that it might be possible instead to convert benzylic α-oxophosphonates to the corresponding benzylic α,α-difluorophosphonates. Accordingly, we arrived at the inventive method for preparing α,α-difluorophosphonates from the corresponding α-oxophosphonates shown in Example II.

Example III

The Example provides for the synthesis of a difluorophosphonomethyl phenylalanine compound (compound 14). In proceeding from compound to compound 11, the method utilizes the novel fluorination step discussed above. Of the compounds shown in Reaction Scheme II, provided in Example III, the compounds numbered 11, 12, 13 and 14 are novel.

Example IV

In this Example, a hydroxy phosphonomethyl phenylalanine compound encompassed by Formula (I) is prepared. The compound is prepared using a direct modification of the synthesis provided in Example I. Compounds 8, 15 and 16 are novel compounds.

Example V

In the Example, a monofluorophosphonomethyl phenylalanine compound encompassed by Formula I is prepared from the corresponding α-hydroxyphosphonate utilizing a nucleophilic fluorinating agent (i.e., DAST).

Example VI

This Example provides an alternative synthesis method for preparing difluorophosphonomethyl phenylalanine compounds encompassed by Formula (I). In the synthesis scheme provided (i.e., VI), the synthesis of compound 27 is analogous to that outlined in Scheme I for the preparation of difluorophosphonate 4', except that 4-bromobenzaldehyde (24) is used rather than the benzaldehyde (1'). Each of the compounds shown in Scheme VI is novel, except for starting compound 24.

Example VII

Compound 10 is prepared based on the inventors' discovery that the corresponding hydroxyphosphono methyl phenylalanine compound 9 can be oxidized to give compound 10. Previous methods of preparing ketophosphonates have relied on the reaction of an appropriate acid chloride with either a trialkylphosphite or the anion of a dialkyl phosphite.

Example VIII

In this Example, the compound diethyl 4-bromo-(oxomethyl)phenyl phosphonate (30) is prepared from the corresponding (hydroxymethyl)phenyl phosphonate (29) using Swern oxidation procedures.

Example IX

In this Example, the compound diethyl (difluoromethyl)phenyl phosphonate (32) is prepared from diethyl benzoyl phosphonate, using a nucleophic fluorinating agent (i.e., DAST).

Example X

In this Example, fluorinated phosphonomethyl phenylalanines are prepared utilizing intermediates having a diethoxy phosphono group thereon, and utilizing mild oxidation procedures.

A. Preparation of Phosphomethyl Phenylalanine Compounds

As disclosed in U.S. patent application Ser. No. 07/767, 621 filed on Sep. 30, 1991 a specific example of the synthesis of a Formula I compound wherein $X=CH_2$ is as follows.

Example I

4[Bis(t-butyl)phosphonomethyl]-N-Fmoc-DL-phenylalanine

Synthesis Overview

Central to the synthesis of the title compound (compound No. 4 in the synthesis below) was the aldol condensation of ethyl α-azidoacetate[7] with 4-[bis(tert-butyl)phosphonomethyl] -benzaldehyde (compound 1) to yield vinyl azide (compound No. 2) (74%). The vinyl azide (compound No. 2) was key to the synthetic route as the tert-butyl groups thereof are retained under the mild conditions (2.8 bar $H_2$/10% Pd.C) employed to effect transformation to the amino ester (compound No. 3). Finally, hydrolysis of the methyl ester with concomitant introduction of the Fmoc-amino protection to yield compound No. 4 was achieved by sequentially treating compound 3 with 1 N sodium hydroxide (20 min.) and thereafter adjusting the pH to 8 by introducing carbon dioxide and allowing the mixture to react overnight with 1-benzotriazolyl-9-fluorenyl-methyl carbonate (Fmoc-OBT).[8] The final product (compound No. 4) was obtained as a white powder (48% overall yield).

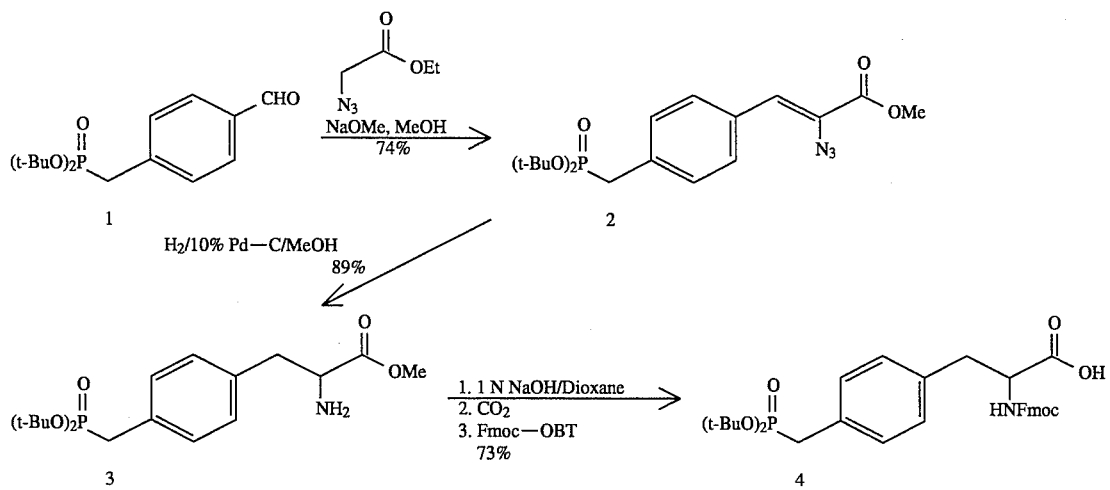

Compound Preparation

α-Azido-4-[bis(tert-butyl)phosphonomethyl]cinnamic acid methyl ester (Compound No. 2)

To a cold (−30° C.) solution of 4-[bis(tert-butyl)phosphonomethyl] benzaldehyde (compound No. 1, 3.12 g, 10 mmol) and ethyl α-azidoacetate (12.90 g, 100 mmol, 10 equiv.) in anhydrous MeOH (50 mL) was added a solution of 5.4M NaOMe (14.8 mL, 80 mmol, 8 equiv.) over 2 minutes under argon with stirring. The colorless reaction mixture was stirred at 2° C. for 1 hour, then diluted with brine (300 mL); extracted with Et20 (3×100 mL); dried (MgSO$_4$) and Et$_2$O removed. The resultant colorless oil was dissolved in pet.ether (30 mL), cooled to −78° C., then warmed to 0° C. with mixing to yield a white crystalline solid. The solid was treated with ice-cold petroleum ether/Et$_2$O (30:1, 30 ml), filtered and dried; yield 2.86 g (74%); mp 109°–111° C. $C_{19}H_{28}N_3O_5P$ MW 409 (compound is too unstable for combustion analysis).

FABMS:m/z=410 (M+1).

IR (KBr) ν=2980, 2124, 1707, 1439, 1369, 1330 cm$^{-1}$.

$^1$H-NMR (200 MHz, CDCl$_3$): δ=1.42 (s, 18H, 2t-C$_4$H$_9$), 3.05 (d, 2H, J=22 Hz, P—CH$_2$), 3.90 (s. 3H, OCH$_3$), 6.90 (s, 1H, vinylic), 7.28 (dd, 2H, J=2 Hz & 8 Hz, ArH$_{3\&5}$), 7.74 (d, 2H, J=8 Hz, ArH$_{2\&6}$).

4-[Bis(tert-butyl)phosphonomethyl]-D,L-phenylalanine methyl ester (Compound No. 3)

A solution of compound 2 (4.50 g, 110 mmol) in MeOH (30 mL) was shaken in a Parr apparatus (2.8 bar H2) over 10%Pd.C (1.10 g) for 1 hour at room temperature. Filtration through Celite filter and removal of solvent yielded compound No. 3 as an oil: 3.75 g (89%).

| $C_{19}H_{32}NO_5P.¾ H_2O$ (385) | calc. found | C 57.20 C 57.23 | H 8.46 H 8.14 | N 3.51 N 3.55 |
|---|---|---|---|---|

FABMS: m/z=386 (M+1)

IR (film) ν=3853, 3383, 2979, 1739, 1653, 1558, 1540, 1514, 1456, 1394, 1369 cm$^{-1}$.

$^1$H-NMR (250 MHz, CDCl$_3$): δ=1.42 (s, 18H, 2t-C$_4$H$_9$), 1.66 (br s, 2H, NH$_2$), 2.86 (dd, 1H,J=8 Hz and 13 Hz, H$_{\beta1}$), 3.01 (d,2H, J=21 Hz, P—CH$_2$), 3.06 (dd, 1H, J=5 Hz and 13 Hz, H$_{\beta2}$), 3.70 (s, 3H, OCH$_3$), 3.72 (dd, 1H, J=5 Hz and 8 Hz, H$_\alpha$), 7.11 (d, 2H, J=8 Hz, ArH$_{2\ and\ 6}$), 7.22 (dd, 2H, J=2 Hz and 8 Hz, ArH$_{3\ and\ 5}$). Structural assignments were supported by $^{13}$C-NMR and DEPT experiments.

4-[Bis(tert-butyl)phosphonomethyl]-N-Fmoc-DL-phenylalanine (Compound No. 4)

A solution of amine compound No. 3 (770 mg, 1.93 mmol) in dioxane (10 mL) was stirred at room temperature (20 min) with aqueous 1 N NaOH (10 mL, 10 mmol, 5 equiv.). Carbon dioxide was then bubbled in (resulting pH=8.0–8.5) and Fmoc-OBT ( 857 mg. 2.40 mmol, 1.2 equiv) was added as a suspension in dioxane (3×10 mL) and stirred overnight at ambient temperature. The reaction mixture was partitioned between cold aqueous 5% citric acid (200 mL) and CHCl$_3$ (3×100 mL); the combined organic was washed with cold 5% citric acid (1×100 mL); brine (1×200 mL); dried (MgSO$_4$) and taken to dryness (that is, the solvent is evaporated away under vacuum) to yield a light yellow resin (1.92 ). The resin was taken up in CHCl$_3$ and filtered through a silica pad. Unreacted Fmoc-OBT and faster impurities were removed with CHCl$_3$ (5×100 mL) with product then being eluted (8×100 mL); with 1% EtOH in CHCl$_3$ and taken to dryness, providing a foam (953 mg) which was dissolved in Et$_2$O (5 mL) and cooled with petroleum ether (20 mL) to yield compound No. 4 as a white powder: 835 mg (73%); mp 65°–70° C. (gas, dec.).

| $C_{33}H_{40}NO_7P$ (593) | calc. found | C 66.77 67.08 | H 6.79 7.26 | N 2.36 2.32 |
|---|---|---|---|---|

FABMS: m/z=594 (M+1).

IR (film) ν=2979, 1721, 1513, 1450, 1370 cm$^{-1}$.

$^1$H-NMR (250 MHz, CDCl$_3$): δ=1.31 (s, 9H,t-C$_4$Hg), 1.38 (s, 9H,t-C$_4$H$_9$), 3.01 (dd, 1H, J=14 Hz and 22 Hz, P—C—H$_\alpha$), 3.13 (dd, 1H, J=14 Hz and 22 Hz, P—C—H$_\beta$), 3.18 (M, 1H, H$_{\delta1}$), 3.29 (m, 1H, H$_{\delta2}$), 4.22 (t, 1H, J=7 Hz, OC—H), 4.32 (dd$^a$, 1H J=7 Hz and 10 Hz, NCO$_2$C—H$_\beta$), 4.48 (dd$^a$, 1H, J=7 Hz and 10 Hz, NCO$_2$C—H$_\beta$), 4.68 (m, 1H, NC—H), 5.40 (d, 1H, J=7 Hz, N—H), 7.12 (d, 2H, J=8 Hz, ArH$_{2\ and\ 6}$), 7.20 (dd, 2H, J=2 Hz and 8 Hz, ArH$_{3\ and\ 5}$), 7.30 (dt$^b$, 2H J=4 Hz and 7 Hz, fluor.-H$_{2\ and\ 7}$)$^c$, 7.39 (t$^b$, 2H, J=7 Hz, fluor.-H$_{3\ and\ 6}$)$^c$, 7.59 (br dd$^{a\ b,\ 2}$H, J=4 Hz and 7 Hz, fluor.-H$_{4\ and\ 5}$)$^d$, 7.76 (br d, 2H, J=7 Hz, fluor.-H$_{1\ and\ 8}$)$^d$. Structural assignments were supported by $^1$H-$^1$H COSY and $^{13}$C-NMR.

$^a$coupling pattern is distorted;
$^b$coupling pattern is apparent;
$^c$assignments may be reversed; and
$^d$assignments may be reversed.

B. Preparation of Benzylic Difluorophosphonates

Exemplary of our general process for the synthesis of benzylic difluorophosphonates is the synthesis of 5'. The process is concerned with the preparation of protected benzylic difluorophosphonates (i.e., 4') by fluorinating the corresponding ketophosphonates (3'). Typical of fluorinating reagents which will accomplish this transformation is (diethylamino)sulfur trifluoride (DAST), However, it is envisioned that other nucleophilic fluorinating agents would also be appropriate. The ketophosphonates can either be prepared by known procedures (for example, the reaction of acid chlorides with either trialkyl phosphites or anions of dialkyl phosphites) or can be prepared from hydroxyphosphonates (2') by oxidation with any of several oxidizing agents. We have found that MnO$_2$, pyridinium dichromate, dichlorodicyanoquinone (DDQ) and the Swern oxidation (dimethyl sulfoxide, oxalyl chloride and triethylamine) all accomplish this oxidation. It is anticipated that several other standard oxidizing agents would also work. Our preparation herein of ketophosphonates by oxidation of the corresponding hydroxyphosphonate (i.e., 2'→3') is novel, and is included as an inventive process in this disclosure.

Scheme I

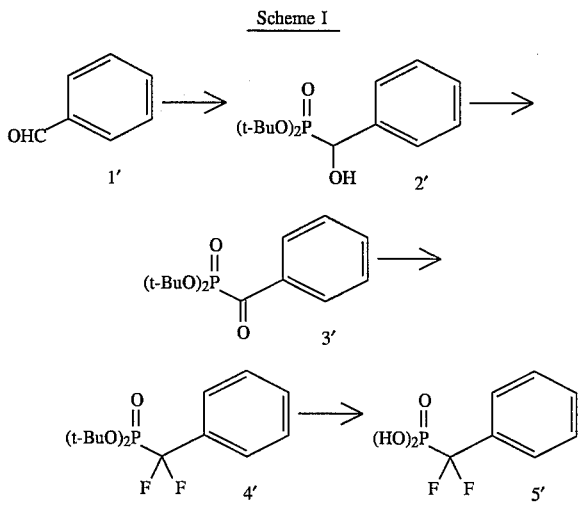

Typical conditions for the preparation of the benzylic difluorophosphonate 5' are:

Preparation of benzylic α-hydroxyphosphonate, 2'

To an ice-cold stirred suspension of NaH (1.2 equiv.; 0.3M in THF) there was added a solution of di-tert-butyl phosphite (1.2 equiv.; 0.3M in THF) over 5 minutes and the mixture was stirred under argon at 0° C. (0.5 hr). A solution of aldehyde 1' (1 equiv.; 1M in THF) was rapidly added and the reaction was then stirred at room temperature (1.5 hr).

The reaction was quenched (H$_2$O), subjected to an extractive workup (brine/CHCl$_3$) and purified by silica gel chromatography, yielding pure benzylic α-hydroxyphosphonate 2' (86%), mp 110°–113° C. (gas).

Preparation of benzylic α-ketophosphonate, 3'

A solution of benzylic α-hydroxyphosphonate 2' (15 mM in toluene) was stirred at reflux with activated MnO$_2$ (10 equiv.; 1.5 hr). The reaction mixture was cooled (0° C.), filtered through celite, taken to dryness and purified by silica gel chromatography to yield pure benzylic α-ketophosphonate 3' (87%), oil.

Conversion of benzylic ketophosphonate 3' to benzylic α,α-difluorophosphonate, 4'

A solution of benzylic α-ketophosphonate 3' (0.5M in DAST) was stirred at room temperature overnight under argon. It was then cooled (0° C.), diluted with CHCl$_3$, added dropwise to cold (0° C.) concentrated KOH, then subjected to an extractive work up and purified by silica gel chromatography to yield pure benzylic difluorophosphonate 4' (79%), oil.

Ester hydrolysis [conversion to benzylic α,α-difluorophosphonic acid, 5']

A solution of di-tert-butyl difluorophosphonate 4' [100 mM in trifluoroacetic acid (TFA)] was stirred at room temperature (1.5 hr) with anisole (5 equiv.). Excess TFA was blown off under argon (gentle warming), with residual traces of TFA being removed under high vacuum. The resulting crude difluorophosphonic acid was crystallized from CHCl$_3$: pet.ether to yield benzylic α,α-difluorophosphonic acid 5' (61%), mp 109°–111° C. (gas; soften 106° C.).

B. Synthesis of the difluorophosphonomethyl phenylalanine 14

Scheme II
Example III

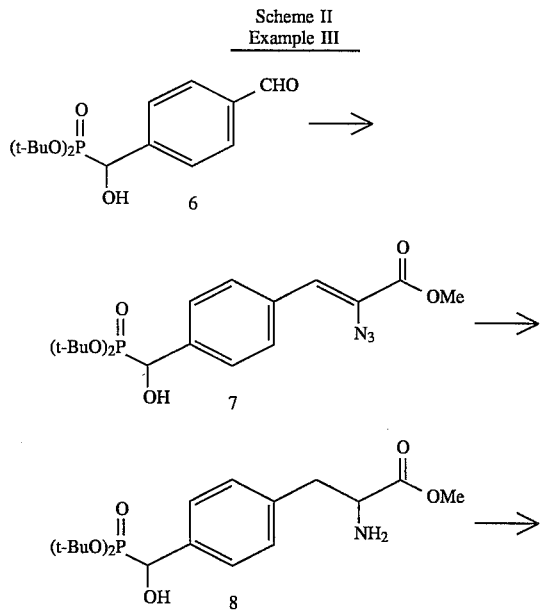

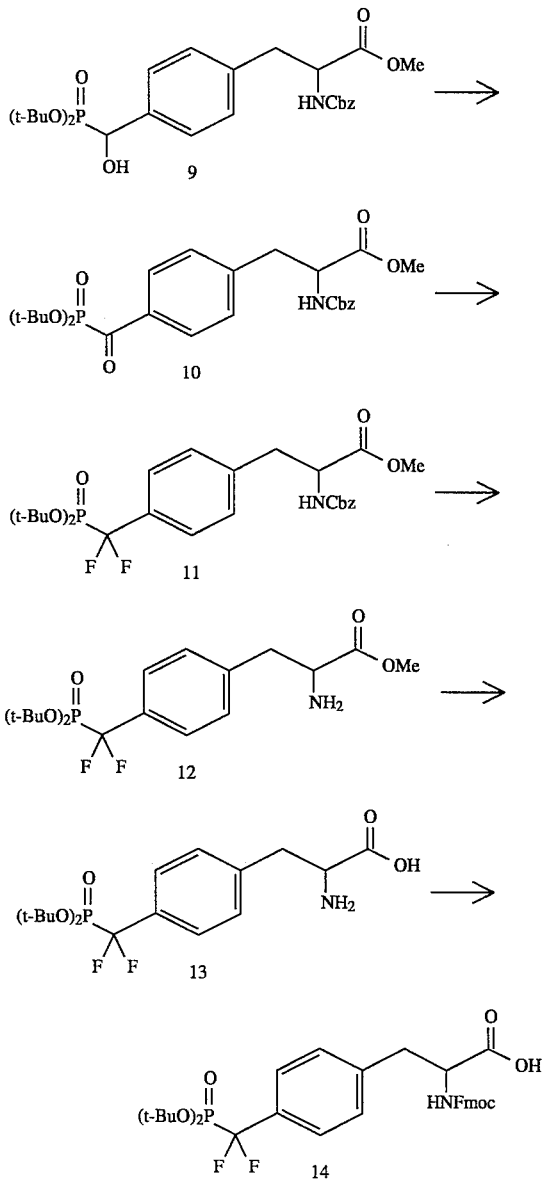

The general process of Example I and the process for preparing benzylic difluorophosphonates outlined in Scheme I of Example II, were applied to the preparation of the difluorophosphonomethyl phenylalanine 14, as shown in Scheme II. In Scheme II "Cbz" indicates a benzyloxycarbonyl group, and "Fmoc" indicates a fluoren- 9-yl-methyloxycarbonyl group.
Experimental conditions for this preparation are given below:

Methyl α-azido-4-[bis(tert-butoxy)phosphorylhydroxymethyl] cinnamate, 7

To a solution of 6.45 g (50 mmol) of ethyl α-azidoacetate and 1.64 g (5.0 mmol) of 4-[bis(tert-butoxy)-phosphorylhydroxymethyl)benzaldehyde 6 in MeOH (20 mL) at −78° C. was added a total of 7.4 mL (40 mmol) of NaOMe, 5.4M in MeOH, dropwise over 5 minutes. The mixture was stirred 5 minutes at −78° C. then an additional 1 hour at 0° C. The resulting light yellow suspension was subjected to an extractive work up (brine/EtOAc) to yield a light yellow crystalline solid, which was triturated with $CHCl_3$/pet.ether (35°–60° C.) to yield 7 as light yellow crystals, 1.26 g (57%), mp 111°–113° C.

Methyl 4-[bis(tert-butoxy)phosphorylhydroxymethyl]-D,L-phenylalaninate, 8

A solution of 7 (1.25 g, 2.85 mmol) in MeOH (50 mL) was hydrogenated in a Parr apparatus over 10% Pd.C (200 mg) under 40 psi $H_2$. The hydrogen was replenished after 10 minutes. The reaction was terminated after 3 hours, and catalyst removed by filtration. Evaporation of solvent yielded 8 as a clear, colorless syrup, 1.17 g (100% crude yield). Silica gel chromatography [$CHCl_3$:MeOH(25:1)] provided pure 8 (92%).

Methyl 4-[bis(tert-butoxy)phosphorylhydroxymethyl]-N-(benzyloxycarbonyl)-D,L-phenylalaninate, 9

To a solution of 8 (876 mg, 2.18 mmol) in THF (22 mL) at 0° C. was added $NEt_3$ (1.22 mL, 8.74 mmol), followed by benzyl chloroformate (0.34 mL, 2.40 mmol) dropwise via syringe. The reaction was stirred at 0° C. for 0.5 hours, then diluted with $Et_2O$ (20 mL) and quenched by dropwise addition of brine (1 mL). Additional brine (20 mL) was added and the organic phase separated and combined with an $Et_2O$ extract (2×20 mL) of the residual brine. The combined $Et_2O$ was dried ($MgSO_4$), filtered and solvent removed by rotary evaporation under reduced pressure to yield crude 9 (1.03 g, 88%). Silica gel chromatography [EtOAc/hexanes (4:3)] provided pure 9 (621 mg, 53%).

Methyl 4-[bis(tert-butoxy)phosphorylcarbonyl]-N-(benzyloxycarbonyl-D,L-phenylalaninate, 10

To a solution of 9 (125 mg, 0.23 mmol) in $CHCl_3$ (1 mL) was added celite (200 mg) and freshly activated 4A molecular sieves (230 mg). Pyridinium dichromate (219 mg, 0.58 mmol) was added and the mixture stirred at ambient temperature (4 hours). The reaction was diluted with EtOAc (5 mL) and filtered through a pad of Florisil (TLC grade). The Florisil was rinsed with EtOAc (30 mL) and combined filtrates taken to dryness by rotary evaporation under reduced pressure to afford crude 10 (85 mg, 70%). Silica gel chromatography [EtOAc/hexanes (1:1)] provided pure 10 (77 mg, 62%).

Methyl 4-[bis(tert-butoxy)phosphoryldifluoromethyl]-N-(benzyloxycarbonyl)-D,L-phenylalaninate, 11

To ketophosphonate 10 (490 mg, 0.92 mmol) was added (diethylamino)sulfur trifluoride (DAST) (1.8 mL) and the mixture stirred overnight at ambient temperature. The reaction mixture was cooled (0° C.), diluted with $CHCl_3$ (5 mL) and added dropwise to a cold, well stirred solution of saturated aqueous $NaHCO_3$ (20 mL). The mixture was extracted with $CHCl_3$ (2×20 mL), dried ($MgSO_4$) and solvent removed by rotary evaporation under reduced pressure to yield crude 11 (665 mg). The crude product was immediately purified by silica gel chromatography [EtOAc/hexanes (1:2)] to provide pure 11 (274 mg, 54%).

Methyl 4-[bis(tert-butoxy)phosphoryldifluoromethyl]-D,L-phenylalaninate, 12

A solution of benzyloxycarbonyl-protected 11 (45 mg, 0.081 mmol) in MeOH (0.8 mL) was stirred at ambient temperature under 1 atm of $H_2$ over 10% Pd, C (9 mg). After 2.5 hours the reaction mixture was filtered through silica gel and taken to dryness in vacuo to yield crude 12 quantitatively. Pure 12 (60% yield) was obtained by silica gel chromatography [$CHCl_3$:MeOH (20:1)].

4-[Bis(tert-butoxy)phosphoryldifluoromethyl]-N-(fluoren- 9-ylmethoxycarbonyl)-D,L-phenylalanine, 14

To a solution of amino ester 12 (15 mg, 0.036 mmol) in dioxane (0.5 mL) was added 1 N NaOH (0.18 mL) and the reaction was stirred at ambient temperature. After 20 minutes, $CO_2$ gas was bubbled into the reaction for 5 minutes, then solid Fmoc-OBt (15 mg, 0.043 mmol) was added and stirring continued for 1 hour. Cold 5% citric acid (10 mL) was added and the mixture was extracted with $CHCl_3$ (3×10 mL); the combined extracts were dried ($MgSO_4$) and the solvent evaporated in vacuo to yield crude 14 (13.7 mg, 60%).

C. Preparation of hydroxyphosphonomethyl phenylalanines

Example IV

Hydroxyphosphonomethyl phenylalanines were prepared using a direct modification of the synthesis provided in Example I. Specifically, compound 8 in Reaction Scheme III was substituted for compound 3 in Example I.

4-[bis(tert-Butoxy)phosphorylhydroxymethyl]-N-(fluoren-9-ylmethoxycarbonyl)-D,L-phenylalaninate (16)

A solution of compound 8 (410 mg, 1.02 mmol) in dioxane (10 mL) was treated with 1 N NaOH (5.1 mL, 5 eq.) and stirred at ambient temperature (0.5 h), yielding a solution of crude 4-[bis(tert-Butoxy)phosphorylhydroxymethyl]-D,L-phenylalanine (15), which was not isolated. The pH was adjusted to 8 by bubbling in $CO_2$ gas, Fmoc-OBT (402 mg, 1.12 mmol) was added and the mixture stirred at ambient temperature (3.5 hours). Ice-cold 5% citric acid (25 mL) was added and the resultant solution was extracted with $CHCl_3$ (3×30 mL). The combined extracts were dried ($MgSO_4$) and evaporated under reduced pressure to yield crude 16. Purification by silica gel chromatography afforded pure 16 as a colorless foam (277 mg, 44%).

D. Preparation of Monofluorophosphonomethyl phenylalanines

Example V

Previously, benzylic α-fluorophosphonates have been prepared from α-hydroxyphosphonates using DAST[13]. We have essentially applied this general chemical transformation to the specific compound 9, leading to monofluorophosphonomethyl phenylalanines 20–23 (Scheme V).

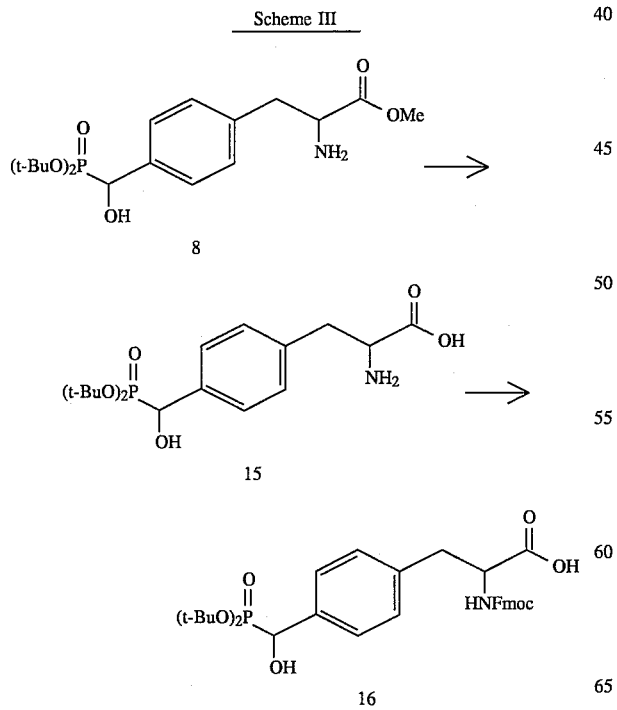

Scheme III

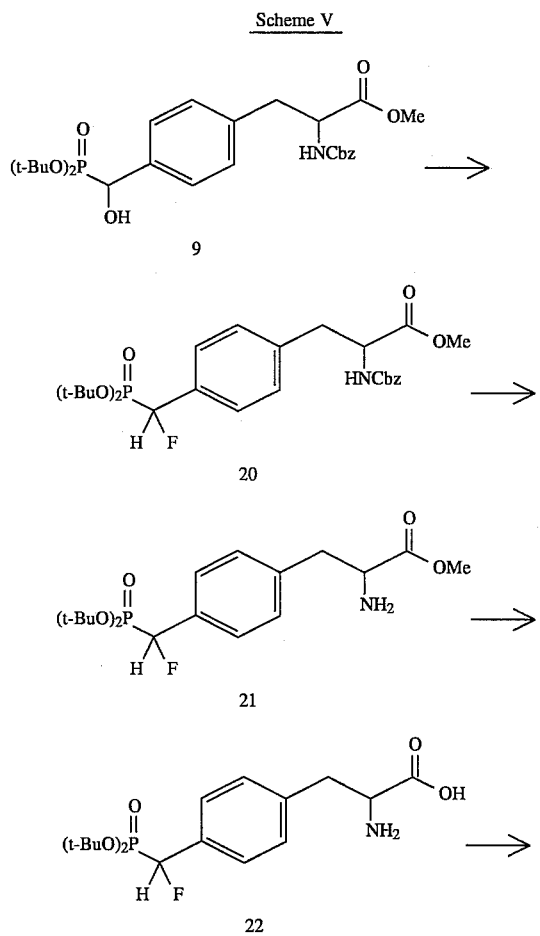

Scheme V

17

-continued
Scheme V

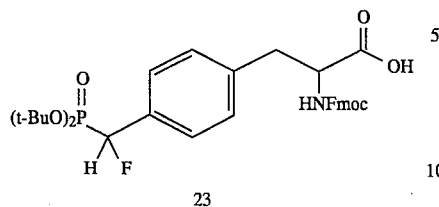

23

Preparation of 23 proceeds from 20 as already described in Example III for the transformation of 11 to 14. Conversion of 9 to 20 applies to this specific case the known transformation of benzylic hydroxyphosphonates to the corresponding monofluorophosphonates.[13]

Methyl 4-[bis(tert-Butoxy)phosphoryl-fluoromethyl]-N-(benzyloxycarbonyl)-D,L-phenylalaninate (20)

To DAST (0.15 mL, 1.1 mmol) in anhydrous CHCl$_3$ (0.6 mL) at −78° C. was slowly added compound 9 (536 mg, 1.0 mmol) in CHCl$_3$ (2.0 mL). After 10 minutes, the reaction mixture was warmed to ambient temperature and stirred (20 minutes). The mixture was slowly diluted with brine (10 mL) then extracted with CHCl$_3$ (2×10 mL) and the combined extracts dried (MgSO$_4$) and evaporated under reduced pressure to yield crude 20 (629 mg). Purification by silica gel chromatography afforded pure 20 as a syrup (295 mg, 55%).

Methyl 4-[bis(tert-Butoxy)phosphoryl-fluoromethyl]-D,L-phenylalaninate (21)

Compound 20 (1.09 g, 2.03 mmol) in anhydrous MeOH (50 mL) was hydrogenated over 10% Pd.C (436 mg) under H$_2$ (45 psi) in a Parr apparatus. The vessel was evacuated and replenished with H$_2$ at approximately 30 minute intervals. After 4 hours, the mixture was removed, filtered through celite and solvent removed under reduced pressure, yielding crude 21 (813 mg). Purification by silica gel chromatography afforded pure 21 (694 mg, 85%).

4-[bis(tert-Butoxy)phosphoryl-fluoromethyl]-N-(fluoren-9-ylmethoxycarbonyl)-D,L-phenylalaninate (23)

To compound 21 (690 mg, 1.71 mmol) in dioxane (17 mL) was added 1 N NaOH (8.6 mL, 5 eq.) and it was stirred at ambient temperature (25 minutes), yielding a solution of crude 4-[bis(tert-Butoxy)phosphorylfluoromethyl] -D,L-phenylalanine (22), which was not isolated. The pH was adjusted to 8 by bubbling in CO$_2$ gas, Fmoc-OBT (673 mg, 1.88 mmol) was added and the mixture stirred at ambient temperature (3 hours). Ice-cold 5% citric acid (30 mL) was added and the resultant solution was extracted with CHCl$_3$ (3×30 mL). The combined extracts were dried (MgSO$_4$) and evaporated under reduced pressure to yield crude 23 (1.48 g). Purification by silica gel chromatography afforded pure 23 as a colorless foam (407 mg, 40%).

18

E. Alternative Synthesis Methods for Synthesizing Difluorophosphonomethyl Phenylalanines

Example VI

Scheme VI

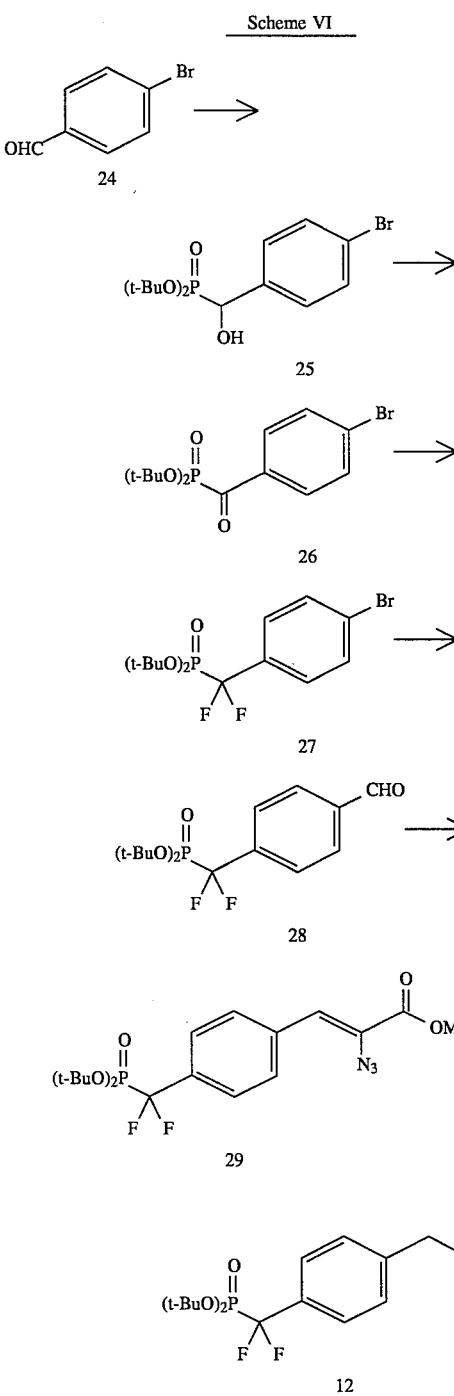

The synthesis of key intermediate 27 is similar to that already described for the synthesis of unsubstituted 4' (Example II). It should be noted, however, that oxidation of bromo hydroxyphosphonate 25 to bromo ketophosphonate 26 must be conducted under milder conditions (pyridinium dichromate 0° C. to room temperature) than those used to oxidize unsubstituted hydroxyphosphonate 2' (MnO$_2$ in refluxing toluene) to avoid decomposition back to the starting aldehyde 24. Transformation of 27 to yield benzaldehyde 28 can be achieved by a number of literature procedures.[14,15]. Once formed, aldehyde 28 can be converted to amino ester 12 using transformations similar to those reported herein (Scheme II) and as disclosed in U.S. application Ser. No. 07/767,621.

4-bis(tert-Butyl)phosphoryl hydroxymethyl]-bromobenzene (25)

To a stirred suspension of NaH, 80% in oil (3.60 g, 2.88 g NaH, 120 mmol) in anhydrous THF (100 mL) at 0° C. there was added tert-butyl phosphite (23.3 g, 120 mmol) dropwise over 5 minutes, and the mixture was stirred at 0° C. (30 minutes). A solution of 4-bromobenzaldehyde (14.52 g, 78 mmol) in anhydrous THF was added rapidly and the mixture stirred at 0° C. (1 hour). The reaction mixture was diluted with $H_2O$ (400 mL), extracted with $CHCl_3$ (1×100 mL) then EtOAc (2×100 mL) and the combined extracts washed with $H_2O$ (1×200 mL), dried ($MgSO_4$) and evaporated under reduced pressure to yield crude 25 as a white crystalline solid. Trituration with pet. ether provided 25 as white crystals (23.92 g, 81%); mp 126.0°–126.5° C.

4-[bis(tert-Butyl)phosphorylcarbonyl]-bromobenzene (26)

To a solution of 25 (16.41 g, 43.3 mmol) in anhydrous $CH_2Cl_2$ (300 mL) at 0° C. was added pyridinium dichromate (40.7 g, 108 mmol, 2.5 eq.) and the suspension was stirred overnight, coming to ambient temperature gradually. The crude mixture was filtered through a 6.5 cm dia×4 cm high pad of florisil having a layer of celite on top, and the pad washed with EtOAc (3×100 mL). The combined filtrates were taken to dryness under reduced pressure to yield 26 as a clear, light brown oil (13.89 g, 86%).

4-[bis(tert-Butyl)phosphoryl difluoromethyl]-bromobenzene (27)

To 26 (12.2 g, 32.4 mmol) was added DAST (8.6 mL, 10.4 g, 64.8 mmol, 2 eq.) over 5 minutes at 0° C. The reaction was then stirred overnight, gradually coming to ambient temperature. The mixture was diluted with $CHCl_3$ (30 mL), cooled and added to a well-stirred solution of $NaHCO_3$ (32.7 g, 390 mmol) in $H_2O$ (300 mL) at 0° C. The resulting mixture was stirred (5 minutes), then extracted with $CHCl_3$ (3×100 mL); the combined organic washed with aqueous NaHCO3 (1×300 mL); dried ($MgSO_4$) and evaporated under reduced pressure to yield crude 27 as a brown oil (12.20 g). Purification by silica gel chromatography afforded pure 27 as a light yellow oil (694 mg, 85%).

4-[bis(tert-Butyl)phosphoryl difluoromethyl]-benzaldehyde (28)

To compound 27 (50 mg, 0.12 mmol) in anhydrous ether (0.63 mL) at −78° C. under argon was added n-BuLi (1.6M in hexanes, 0.12 mL, 0.19 mmol) and the mixture was stirred at −78° C. (20 minutes). A solution of ethyl formate, 1M in ether (0.25 mmol, 2 eq.) was added and the mixture stirred (0.5 hours at −78° C.). Saturated aqueous $NH_4Cl$ (1 mL) was added and the mixture warmed to ambient temperature and extracted with ether (3×1 mL). The combined extracts were dried ($MgSO_4$) and taken to dryness under reduced pressure, affording 43 mg of crude 28, however, contaminated with starting material 27.

F. Preparation of Ketophosphone phenylalanines

Example VII

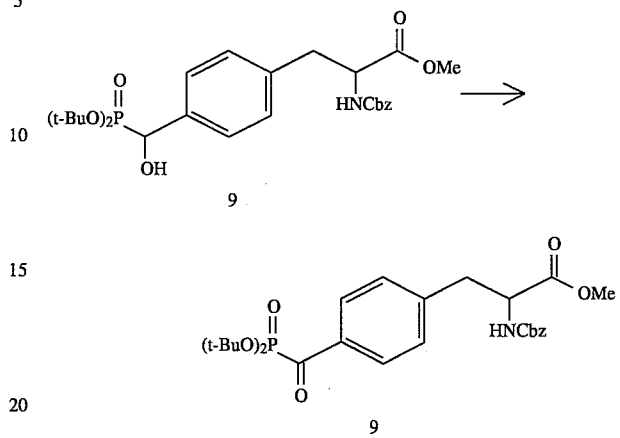

compound 10 is prepared based on the inventors' discovery that the corresponding hydroxyphosphono methyl phenylalanine compound 9 can be oxidized to give compound 10.

G. Preparation of diethyl 4-bromo(oxomethyl)phenyl phosphonate

Example VIII

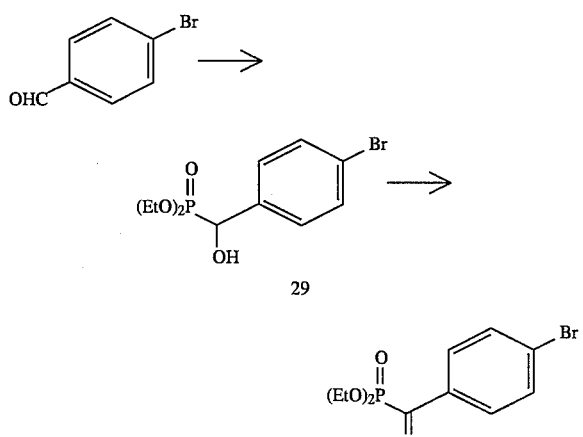

Diethyl 4-bromo-(hydroxymethyl)phenyl phosphonate (29)

To NaH (97%, 103 mg, 4.3 mmol) in THF (14 mL) at 0° C. under argon was added diethyl phosphite (0.50 mL, 3.9 mmol) in THF (4 mL) dropwise. After stirring for 30 minutes, 4-bromo benzaldehyde (Aldrich, 722 mg, 3.9 mmol) in THF (2 mL) was added slowly and the solution was stirred at room temperature (30 minutes). The reaction was quenched with a few drops of brine, then partitioned between brine (50 mL) and $CHCl_3$ (50 mL). The brine was acidified with 6 N HCl, the layers separated, and the aqueous layer was washed with $CHCl_3$ (2×20 mL). After drying the combined $CHCl_3$ washes ($MgSO_4$) and removal of the solvent in vacuo, crude 29 was obtained (1.14 m) as a colorless oil. Purification via silica gel chromatography (gradient elution with hexanes/EtOAc, 1:1, 1:2, 1:3, 0:1) afforded 930 mg (74%) of 29 as an oil which crystallized on standing. $^1$H NMR (CDCl$_3$) δ 7.47 (d, 2H, J=8.5 Hz, H$_3$ and H$_5$), 7.34 (dd, 2H, J= 8.5, 2.2 Hz, H$_2$ and H$_6$), 4.96 (d, 1H, J=10.8 Hz, PCH), 4.05 (m, 4H, POCH$_2$), 1.24 (t, 6H, J=7.2 Hz, CH$_3$).

Diethyl 4-bromo-(oxomethyl)phenyl phosphonate (30)

This compound was prepared by exploiting an oxidation procedure as set forth in Taber, D. F.; Amedio, J. C., Jr.; Jung, K-Y. J. Org. Chem. 1987, 52, 5621–5622. There was no indication in our prior experiments or the literature that any particular oxidative condition would work in the synthesis of this model compound, or of other diethylbenzylic phosphonates. Surprisingly, the following set of conditions work in the synthesis of the compound.

To compound 29 (25 mg, 0.077 mmol) in CH$_2$Cl$_2$ (0.4 mL) at 0° C. under argon was added DMSO (0.01 mL, 0.15 mmol) and then P$_2$O$_5$ (22 mg, 0.15 mmol). After stirring for 20 minutes at room temperature, the solution was cooled to 0° C., Et$_3$N (0.04 mL, 0.27 mmol) was added dropwise, and stirring was maintained overnight. The reaction was partitioned between H$_2$O (2 mL) and CH$_2$Cl$_2$ (2 mL), acidified with 1 N HCl, and the layers separated. The HCl layer was washed with CH$_2$Cl$_2$ (2 mL) and the combined CH$_2$Cl$_2$ washes were extracted with brine, dried (MgSO$_4$), and evaporated to give a crude mixture (20 mg) of compound 29, compound 30, and decomposition material. The presence of 30 was confirmed by $^1$H NMR and TLC analysis.

H. Preparation of diethyl(difluoromethyl)phenyl phosphonate

Example IX

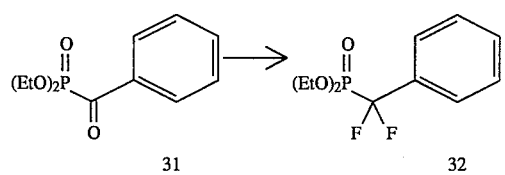

Diethyl (difluoromethyl)phenyl phosphonate (32)

To diethyl benzoyl phosphonate (Terauchi, K.; Sakurai, H. Photochemical studies of the esters of aroyl-phosphonic acids. Bull. Chem. Soc. Jpn. 1970, 43, 883– 890) 31 (242 mg, 1.0 mmol) at RT under argon was slowly added DAST (0.66 mL, 5.0mmol) and the resulting mixture was stirred at room temperature overnight. After cooling to 0° C., CHCl$_3$ (1 mL) was added and then the excess DAST was quenched with ice cold brine (2 mL). The brine was then washed with CHCl$_3$ (2 mL), the CHCl$_3$ was dried (MgSO$_4$), and evaporated in vacuo to give 293 mg of crude 32. Silica gel chromatography (hexanes/EtOAc, 3:1) afforded pure 32 (130 mg, 49%) as a colorless, viscous oil. $^1$H NMR (CDCl$_3$) δ 7.60 (m, 2H), 7.45 (m, 3H), 4.16 (m, 4H, POCH$_2$), 1.29 (t, 6H, J=7.11 Hz, CH$_3$). Anal. Calcd. for C$_{11}$H$_{15}$O$_3$F$_2$P: C, 50.01; H, 5.72. Found: C, 50.25; H, 5.77.

I. Preparation of fluorinated phosphonomethyl phenylalanines

Example X

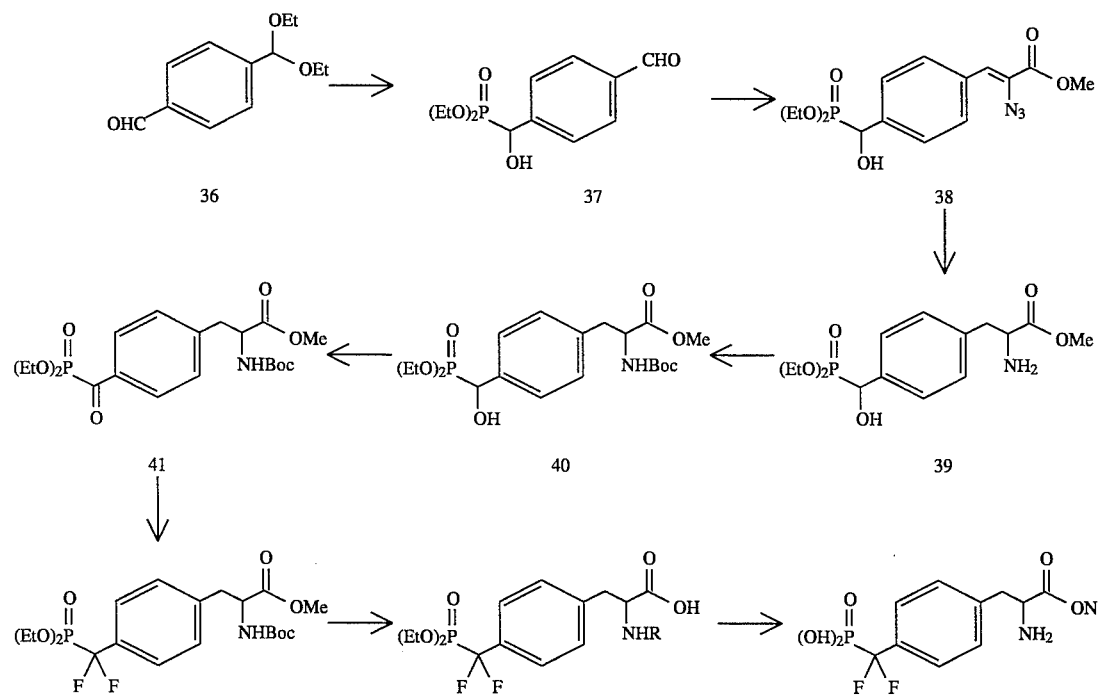

4-[[(Di-ethoxy)phosphono]hydroxymethyl]-benzaldehyde (37)

A total of 12.9 mL (13.8 g, 100 mmol) of diethyl phosphite was added to a stirring suspension of 3.30 g (110 mmol) of NaH, 80% in oil in 200mL dry THF under argon at 0° C., and the reaction stirred at 0° C. (45 minutes). To this was added aldehyde 36 (18.7 g, 90 mmol) and the reaction continued on ice (1 hour). The mixture was diluted with $H_2O$ (50 mL) and 37% HCl (20 mL), then concentrated by rotary evaporation (30° C.). The resulting opaque oil was diluted with $H_2O$ (500 mL); extracted with EtOAc (2×250 mL); washed with brine (1× 500 mL); dried ($MgSO_4$) and rotovapped (35 C) to dryness. The resulting oil was crystallized from cold ether to yield 37 as white crystals (9.0 g., 37%), mp 78.5°–80.5° C. $^1$H NMR (250 MHz, DMSO-$d_6$) δ: 10.01 (s, 1H, CHO), 7.90 (d, 2H, J=8.1 Hz, aromatic), 7.65 (dd, 2H, J=8.1, 2.0 Hz, aromatic), 6.43 (dd, 1H, J=14.9, 5.7 Hz, OH), 5.12 (dd, 1H, J=15.0, 5.6 Hz, P—CH), 3.98 (m, 4H, $OCH_2$), 1.17 (t, 6H, J=7.0 Hz, $CH_3$); mp 78.5°–80.5° C.; FABMS m/z 271.1 (M–H)–.

Methyl α-azido-4-[[(Diethoxy)phosphono]hydroxymethyl]-cinnamate (38)

To a dry 1 L round bottom flask was added 10.9 g (40 mmol) of 37, 52 g (400 mmol, 10 equivalents) of ethyl α-azidoacetate and 200 mL of anhydrous MeOH and the solution stirred under argon at –78° C. To this was added via syringe over 10 minutes, 59 mL (320 mmol, 8 equivalents) of NaOMe, 5.4M in MeH. The reaction was stirred briefly (5 minutes) at –78° C., then at 0° C. (1 hour). The yellow suspension was partitioned between ice-cold brine (400 mL) and EtOAc (3×250 mL). The combined EtOAc was washed with brine (1×400 mL); dried well ($MgSO_4$) and rotovapped (20° C.) to a light yellow solid. Trituration with ether:petroleum ether (35°–60° C.) provided 38 as a light yellow solid (7.72 g, 52%), mp 106°–110° C. $^1$H NMR (250 MHz, DMSO-$d_6$) δ: 7.86 (d, 2H, J= 8.2 Hz, aromatic), 7.48 (dd, 2H, J=8.2, 1.8 Hz, aromatic), 6.95 (s, 1H, vinylic), 6.30 (dd, 1H, J= 15.3, 5.5 Hz, OH), 5.01 (dd, 1H, J=14.3, 5.5 Hz, P—CH), 3.98 (m, 4H, $OCH_2$), 3.87 (s, 3H, $CO_2CH_3$), 1.18 (t, 3, J=7.0 Hz, $CH_3$), 1.16 (t, 3H, J=7.0 Hz, $CH_3$); mp 106°–110° C. (dec).

Methyl 4-[[(Di-ethoxy)phosphono]hydroxymethyl]-D,L-phenylalaninate (39)

A total of 3.4 g (9.2 mmol) of 38 in 100 mL MeOH was hydrogenated at 40 psi $H_2$ over 300 mg 10% Pd.C. Hydrogen was replenished at t=15, 60, 135, 210 and 255 minutes and 300 mg additional 10% Pd, C was added at t=135 and 255 minutes and the reaction terminated at t=6 hours. The mixture was filtered through celite and rotovapped (30° C.) to yield 39 as a clear colorless oil (2.97 g, 95%). The oil crystallized from ether yielding white crystals, mp 94°–100° C. (soften 77° C.). $^1$H NMR (250 MHz, DMSO-$d_6$) δ: 7.34 (d, 2H, J=7.5 Hz, aromatic), 7.15 (d, 2H, J=7.5 Hz, aromatic), 6.16 (br s, 1H, OH), 4.89 (d,1H, J=13.0 Hz, PCH), 3.93 (m, 4H, $OCH_2$), 3.59 (m, 1H, $H_α$), 3.57 (s, 3H, $CO_2CH_3$), 2.87 (dd, 1H, J=13.4, 6.7 Hz, $H_β$), 2.76 (dd, 1H, J=13.4, 7.2 Hz, $H_β$), 1.17 (t, 3H, J=7.0 Hz, $CH_3$), 1.13 (t, 3H, J=7.0 Hz, $CH_3$), mp 94°–100° C.; FABMS m/z 346.1 (M+H)+.

Methyl 4-[[(Di-ethoxy)phosphono]hydroxymethyl]-N-(tert-butoxycarbonyl)-D,L-phenylalaninate (40)

To a stirred suspension of 862 mg (2.5 mmol) of 39 in anhydrous THF (15 mL) was added a solution of di-[(tert-butoxy)dicarbonyl] (654 mg, 3.0 mmol, 1.2 equivalents) in 2×5 mL THF dropwise over 3 minutes at 0° C. argon. The suspension was then stirred on ice and allowed to come to room temperature and stirred overnight. The resulting mixture was rotovapped (20° C.) to a syrup, taken up in $CHCl_3$, applied to a 6.5 cm diameter×3 cm high 5– 25μ silica pad wet with petroleum ether (35°–60° C.) and eluted first with $CHCl_3$ to remove unreacted reagent. Product was then eluted with EtOAc, to yield after rotary evaporation, 40 as a white foam (1.03 g, 93%).

$^1$H NMR (250 MHz, $CDCl_3$) δ: 7.36 (dd, 2H, J=8.1, 2.0 Hz, aromatic), 7.07 (d, 2H, J=8.1 Hz, aromatic), 4.93 (dd, 1H, J=10.7, 4.8 Hz, P—CH), 4.88 (br s, 1H, NH), 4.51 (m, 1H, He), 3.96 (m, 4H, $OCH_2$), 3.64 (s, 3H, $CO_2CH_3$), 3.31 (dd, 1H, J=10.0, 4.8 Hz, OH), 3.02 (m, 2H, $H_β$), 1.66 (s, 9H, $C(CH_3)_3$), 1.19 (2 t, 6H, J=7.4, 7.0 Hz, $CH_3$); FABMS m/z 446.1 (M+H)+.

Methyl 4-[[(Di-ethoxy)phosphono]ketomethyl]-N-(tertbutoxycarbonyl)-D,L-phenylalaninate (41)

To a solution of oxalyl chloride (371 μL, 548 mg, 4.32 mmol, 2 equivalents) in anhydrous $CH_2Cl_2$ (8 mL) at –78° C. under argon was added anhydrous DMSO (612 μL, 674 mg, 8.64 mmol, 4 equivalents) in anhydrous $CH_2Cl_2$ (8 mL) dropwise over 17 minutes. To the resulting clear, colorless solution was added 40 (961 mg, 2.16 mmol) in anhydrous $CH_2Cl_2$ (8 mL) dropwise at –78° C. over 15 minutes. The reaction was stirred at –78° C. (45 minutes) then $NEt_3$ (3.00 mL, 2.18 g, 21.6 mmol, 10 equivalents) in anhydrous $CH_2Cl_2$ (8 mL) was added dropwise at –78° C. over 10 minutes. The resulting clear, light yellow solution was stirred at 0° C. (50 minutes), then shaken well with ice-cold 0.2 N HCl/brine (100 mL); extracted with EtOAc (3×75 mL); washed with ice-cold 0.2 N HCl/brine (2×50 mL); brine (2×100 mL); dried ($MgSO_4$) and rotovapped (20° C.) once from $CHCl_3$, then twice from $CH_2Cl_2$ and placed under high vacuum, yielding 41 as an oil (962 mg, 100%).

$^1$H NMR (250 MHz, $CDCl_3$) δ: 8.14 (d, 2H, J=7.9 Hz, aromatic), 7.21 (d, 2H, J=7.9 Hz, aromatic), 4.96 (d, 1H, J=7.7 Hz, NH), 4.56 (m, 1H, $H_α$), 4.21 (2 q, 4H, J=7.0 Hz, $OCH_2$), 3.67 (s, 3H, $CO_2CH_3$), 3.10 (m, 2H, $H_δ$), 1.35 (s, 9H, $C(CH_3)_3$), 1.32 (t, 6H, J=7.0 Hz, $CH_3$); FABMS m/z 443.3 (M·)–.

Methyl 4-[[(Di-ethoxy)phosphono]difluoromethyl]-N-(tertbutoxycarbonyl)-D,L-phenylalaninate (42)

To a total of 935 mg (2.0 mmol) of 41 at –78° C. was added ice-cold DAST (1.32 mL, 1.62 g, 10.0 mmol, 5 equivalents) neat under argon. The mixture was then swirled at room temperature until homogeneous, then the light yellow solution was stirred on an ice bath and allowed to come to room temperature gradually while stirring overnight. The solution was diluted with $CHCl_3$ (20 mL), cooled and added dropwise under argon with stirring to an ice-cold saturated aqueous NaHCO3 solution (200 mL). The mixture was then extracted with EtOAc (150 mL; 2×75 mL); washed with ice-cold aqueous $NaCO_3$ (1×100 mL); ice-cold 0.2 N HCl/brine (2×100 mL); brine (2×100 mL); dried ($MgSO_4$) and rotovapped (20° C.) to yield crude 42 as clear yellow syrup (820 mg, 88% crude yield). The syrup was purified by silica gel chromatography using first $CHCl_3$, then 2%

EtOAc in CHCl$_3$ to yield pure 42 as a light yellow syrup (583 mg, 62%).

$^1$H NMR (250 MHz, CDCl$_3$) δ: 7.48 (d, 2H, J=7.8 Hz, aromatic), 7.16 (d, 2H, J=7.8 Hz, aromatic), 4.91 (d, 1H, J=7.7 Hz, NH), 4.53 (m, 1H, H$_β$), 4.10 (m, 4H, OCH$_2$), 3.64 (s, 3H, CO$_2$CH$_3$), 3.06 (m, 2H, H$_β$), 1.35 (s, 9H, C(CH$_3$)$_3$), 1.23 (t, 6H, J=7.2 Hz, CH$_3$); FABMS m/z 466.1 (M+H)+.

4-[[(Di-ethoxy)phosphono]difluoromethyl]-N-(tertbutoxycarbonyl)-D,L-phenylalanine (33)

To a solution of 42 (536 mg, 1.15 mmol) in THF (10 mL) at 0° C. was added 0.2 N LiOH (6.3 mL, 1.3 mmol, 1.1 equivalents) at 0° C. dropwise over 15 minutes. The reaction was then stirred at 0° C. and monitored by TLC with four additions of 576 μL (0.115 mmol, 0.1 equivalents) 0.2 N LiOH over a 2 hour period. The reaction mixture was then partitioned between ice-cold 0.2 N HCl/brine and EtOAc (3×75 mL); dried (MgSO$_4$) and solvent removed by rotovap (20° C.) to yield 33 as a foam (500 mg, 96%). 1H NMR (250 MHz, CDCl$_3$+D$_2$O) δ:7.46 (d, 2H, J=8.1 Hz, aromatic), 7.21 (d, 2H, J=8.1 Hz, aromatic), 4.57 (m, 1H, H$_α$), 4.10 (m, 4H, OCH$_2$), 3.11 (m, 2H, H$_β$), 1.36 (s, 9H, C(CH$_3$)$_3$), 1.23 (2 t, 6H, J=7.1 Hz, CH$_3$); FABMS m/z 452.1 (M+H)+.

4-[[Di-ethoxy)phosphono]difluoromethyl]-N-(fluorenylmethoxycarbonyl)-D,L-phenylalanine (34)

A solution of 33 (100 mg, 0.22 mmol) in TFA (500 μL) was stirred at 0° C. under argon (1 hour), taken to dryness by rotary evaporation (20° C.), then taken to dryness from 3× 1 mL CH$_2$Cl$_2$ and placed under high vacuum to yield a foam. This was taken up in dioxane (1 mL) to which was added Fmoc-OSu (67 mg, 0.2 mmol, 0.9 equivalents) and a solution of NaHCO$_3$ (74 mg, 0.88 mmol, 4 equivalents) in H$_2$O (1 mL) and the mixture stirred at room temperature 2 hours. The reaction was diluted with ice-cold 0.2 N HCl/brine (25 mL) and extracted with EtOAc (3×50 mL); washed with 0.2 N HCl/brine (2×25 mL); dried (MgSo$_4$) and taken to dryness by rotary evaporation, then placed under high vacuum to yield crude 34 as a foam (131 mg). The foam was purified by silica gel chromatography using first CHCl$_3$, then 2% EtOAc and finally EtOAc, yielding 34 as a white foam (87 mg, 77%). $^1$H NMR 250 MHz, CDCl$_3$.) δ: 7.68 (d, 2H, J=7.3 Hz, fluorenyl H$_{1'}$, H$_{8'}$), 7.49 (d,2H, J=7.3 Hz, fluorenyl H$_{4'}$, H$_{5'}$), 7.44 (d, 2H, J= 7.8 Hz, aromatic), 7.33 (t, 2H, J=7.3 Hz, fluorenyl H$_{3'}$, H$_{6'}$), 7.23 (t, 2H, J=7.3 Hz, fluorenyl H$_{2'}$, H$_{7'}$), 7.13 (d, 2H, J=7.8 Hz, aromatic) , 5.35 (d, 1H, J=7.7 Hz, NH), 4.62 (m, 1H, H$_α$), 4.42 (dd, 1H, J=10.6, 7.1 Hz, fluorenyl H$_{9'}$), 4.30 (dd, 1H, J=10.6, 7.1 Hz, NCO$_2$CH), 4.10 (m, 5H, POCH$_2$& NCO$_2$CH), 3.13 (d, 2H, J= 5.5 Hz, H$_β$), 1.21 (2 t, 6H, J=7.1 Hz, CH$_3$); FABMS m/z 574.2 (M+H)+.

4-(Phosphono) difluoromethyl-D,L-phenylalanine (35)

A total of 100 mg (0.22 mmol) of 33 in 3 N HCl was stirred at reflux (4 hours), then mixed briefly with a spatula tip of activated charcoal and filtered through celite. Removal of solvent by rotary evaporation (45° C.) yielded 35 as a cream colored solid (66 mg, 93%), mp> 300° C. (dec). $^1$H NMR (250 MHz, DMSO-d$_6$+D$_2$O) δ: 8.20 (s, 2H, NH$_2$), 7.89 (d, 2H, J=8.0 Hz, aromatic), 7.38 (d, 2H, J=8.0 Hz, aromatic), 4.16 (t, 1H, J=6.5 Hz, H$_α$), 3.15 (d, 2H, J=6.5 Hz, H$_β$); mp>300° C.; FABMS m/z 296.0 (M+H)+.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein is expressly incorporated herein by reference in its entirety.

REFERENCES

1. Marseigne, I.; Roques, B. P. Synthesis of new amino acids mimicking sulfated and phosphorylated tyrosine residues. J. Org. Chem., 1988, 53, 3621– 3624.

2. Bigge, C. F.; Drummond, J. T.; Johnson, G.; Malone, T.; Probert, A. W., Jr.; Marcoux, F. W.; Coughenour, L. L.; Brahce, L. J. Exploration of phenyl-spaced 2 -amino-(5,9)-phosphonoalkanoic acids as competitive N-methyl-D-aspartic acid antagonists. J. Med. Chem., 1989, 32, 1580–1590.

3. Bayle-Lacoste, M.; Moulines, J.; Collignon, N.; Boumekouez, A.; de Tinguy-Moreaud, E.; Neuzil, E. Synthesis of 4-phosphono-DL-phenylalanine and of 4 -(phosphonomethyl)-DL-phenylalanine, two analogues of O-phosphotyrosine. Tetrahedron, 1990, 46, 7793– 7802.

4. Roques, B. P.; Marseigne, I.; Charpentier, B. Preparation of amino acids and tyrosine-containing peptides as drugs and pharmaceutical compositions containing them. Eur. Pat. Appl. EP 354 108 (CA 113: 78979x), 1990.

5. Carpino, L. A.; Han, G. Y. The 9-fluorenylmethoxycarbonyl function, a new base-sensitive amino-protecting group, J. Amer. Chem. Soc., 1970, 92, 5748–5749.

6. Burke, T. R.; Knight, M.; Chandrasekhar, B. Solid-phase synthesis of viscosin, a cyclic depsipeptide with antibacterial and antiviral properties. Tetrahedron Letters, 1989, 30, 519–522.

7. Hemetsberger, H.; Knittel, D.; Weidmann, H. Montgh. Chem., 1969, 100, 1599–1603.

8. Paquet, A. Can. J. Chem., 1982, 60, 976–80.

9. Sealock, R. R. D-Tyrosine in Biochemical Preparations, Vol. I, John Wiley & Sons, Inc., London, England, (H. E. Carter, Ed.), 1949, 71–74.

10. Differding, E.; Duthaler, R. O.; Krieger, A.; Rüegg, G. M.; Schmit, C. Electrophilic Fluorinations with N-fluorobenzenesulfonimide: Convenient access to α-fluoro- and α,α-difluorophosphonates; Synlett 1991, 395–396.

11. Middleton, W. J.; Bingham, E. M. α,α-Difluoroarylacetic acids: Preparation from (diethylamino) sulfur trifluoride and α-oxoarylacetates. J. Org. Chem., 1980, 45, 2883–2887.

12. Burke, T. R. Jr., Li, Z. H.; Bolen, J. B.; Marquez, V. E., Phosphate-containing inhibitors of tyrosine-specific protein kinases. J. Med. Chem., 1991, 34 1577–1581.

13. Blackburn, G. M.; Kent, D. E. Synthesis of alpha- and gamma-fluoroalkylphosphonates. J. Chem. Soc. Perkin. Trans. 1986, 1, 913–917.

14. Mignani, G.; Kramer, A.; Puccetti, G.; Ledoux, I.; Zyss, J.; Soula, G. Effect of a weak donor on the intramolecular charge-transfer of molecules containing 2 neighboring silicon atoms. Organo-metallics 1991, 10, 3656–3659.

15. Hartman, G. D.; Halczenko, W. A convenient synthesis of 4-aminomethyl-L-phenylalanine. Synth. Commun. 1991, 21, 2103–2107.

16. Bozell, J. J.; Vogt, C. E.; Gozum, J. Transition-metal-assisted asymmetric synthesis of amino acid analogues. A new synthesis of optically pure D- and L-pyridylalanines. J. Org. Chem., 1991, 56, 2584–2587.

17. Terauchi, K.; Sakurai, H. Photochemical studies of the esters of aroylphosphonic acids. Bull. Chem. Soc. Jpn. 1970, 43, 883–890.

18. Scherer, H.; Hartmann, A.; Regitz, M.; Tunggall, B. D.; Gunther, H. 7-Phosphono-7-aryl-norcaradiene. Chem. Ber. 1972, 105, 3357–3381.

What is claimed is:

1. The compound methyl 4-(((di-ethoxy)phosphono)difluoromethyl)-N-(tertiary butoxycarbonyl)-D,L-phenylalaninate.

2. The compound 4-(((di-ethoxy)phosphono)difluoromethyl)-N-(tertiary butoxycarbonyl)-D,L-phenylalanine.

3. The compound 4-(((di-ethoxy)phosphono)difluoromethyl)-N-(fluorenylmethoxycarbonyl)-D,L-phenylalanine.

* * * * *